(12) United States Patent
Petitjean

(10) Patent No.: US 9,879,213 B1
(45) Date of Patent: Jan. 30, 2018

(54) BIOSOLIDS STORAGE SYSTEM

(71) Applicant: John Petitjean, Bradford, OH (US)

(72) Inventor: John Petitjean, Bradford, OH (US)

( * ) Notice: Subject to any disclaimer, the term of this patent is extended or adjusted under 35 U.S.C. 154(b) by 0 days.

(21) Appl. No.: 15/269,316

(22) Filed: Sep. 19, 2016

(51) Int. Cl.
*C12M 1/00* (2006.01)
*C12M 1/34* (2006.01)
*C12M 1/36* (2006.01)
*C05F 17/02* (2006.01)
*G01N 33/00* (2006.01)

(52) U.S. Cl.
CPC ............ *C12M 23/14* (2013.01); *C05F 17/027* (2013.01); *C05F 17/0211* (2013.01); *C05F 17/0282* (2013.01); *C12M 41/34* (2013.01); *C12M 41/48* (2013.01); *G01N 33/0057* (2013.01)

(58) Field of Classification Search
CPC ...... C12M 23/14; C12M 41/34; C12M 41/48; G01N 33/0057; C05F 17/027; C05F 17/0282; C05F 17/0211
See application file for complete search history.

(56) References Cited

U.S. PATENT DOCUMENTS

| | | | |
|---|---|---|---|
| 7,005,991 B1* | 2/2006 | Des Clers | G01N 25/54 340/506 |
| 2013/0125620 A1* | 5/2013 | Ovadia | G01N 30/08 73/23.39 |

* cited by examiner

*Primary Examiner* — Sally A Merkling
(74) *Attorney, Agent, or Firm* — R. William Graham

(57) ABSTRACT

A system reduces and/or prevents the risk of spontaneous ignition and/or explosion of an explosive atmosphere which uses a bag, sealable couplings, automated valves, an explosive gas detector operably disposed inside the bag and in communication with a processor which when the explosive gas detector detects gas levels of an explosive type gas and of a second predetermined molecular weight different than the first predetermined molecular weight and at level to present a risk, the processor causes actuation of the automatically controlled valve to open and release the inert gas into the bag which in turn drives the explosive gas out through one way check valve by means of the different molecular weights.

3 Claims, 1 Drawing Sheet

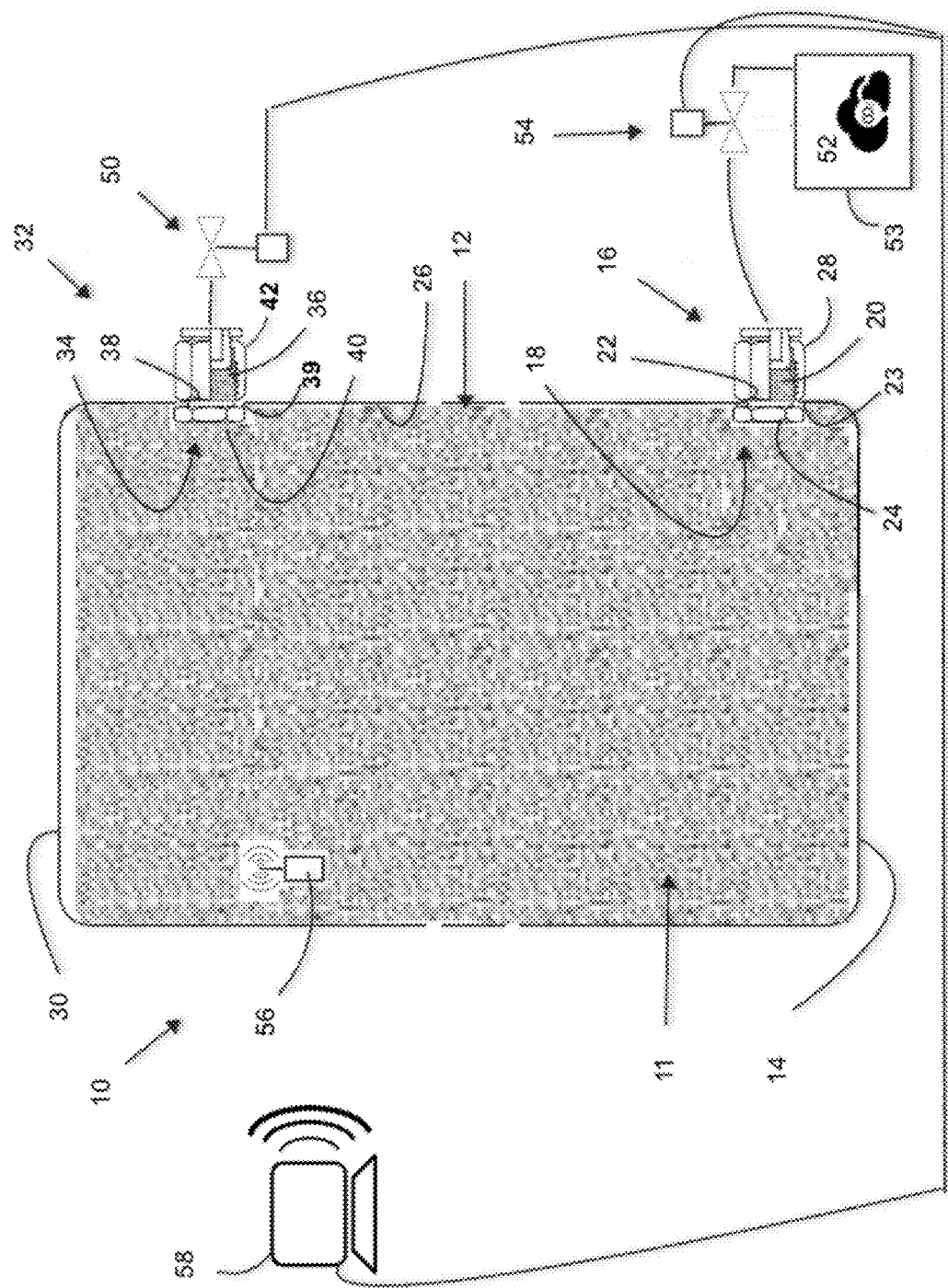

BIOSOLIDS STORAGE SYSTEM

FIELD OF INVENTION

The present invention relates to a system for aiding in preventing potential spontaneous ignition and/or explosion in the containment of biomass which can occur from flammable substances in the form of gases, vapors, mists, dusts and combustible fertilizer.

PRIOR ART

Biosolids are commonly stored in large biomass bags and are transported locally in enclosed trucks to control odors and noise. Upon arriving at a land application site, they are either directly applied to the land using tractors, tank wagons, irrigation systems or special application vehicles or stored in silos. In the case of silo storage, there is a limited time in which the material can sit before causing a hazardous condition. Every year, fires and/or explosions occur from improper storage and use of such material.

Typically, air with one or more flammable substances, such as methane, can result in explosion or ignition when they are stored at ambient or higher temperatures in confined or semi-confined environments. Unmaintained silos present an ideal environment for such explosions to occur wherein explosive atmospheres include hydrocarbons and air. Thus, it is important to reduce and hopefully eliminate the risk of explosion of these explosive atmospheres.

Various processes and devices exist for determining what environmental conditions can cause an explosion. The processes and devices sense elements within the environment and then determine if the levels are an explosive risk.

There is a need for reducing the risk of such explosions as well as providing a device for minimizing the risk of explosion in storing such material. Also, there is a desire to extend the time in which such materials require use.

SUMMARY OF INVENTION

It is an object to improve biosolids containment.

A further object is to prevent and/or minimize risk of explosion in the storage of biosolids material.

Yet another object is to provide a system for storing biosolids in a manner to reduce the risk of spontaneous ignition and/or explosion.

Still another object is to increase the potential storage time of contained biosolids material.

Accordingly, the present invention relates to a biosolids storage system. The system reduces and/or prevents the risk of spontaneous ignition and/or explosion of an explosive atmosphere. The system includes a biosolids bag for containing a biosolids material fertilizers. Connected to a lower portion of the bag is a first removable coupling having a male part having a male end extending through an opening in the lower portion of the bag and a collar which abuts an inner side of the bag when the male end is fully inserted therethrough. The first removable coupling has a female part removably connected to the male end in a manner to sealably connect and sandwich a part of the lower portion between the collar and female part. To an upper portion of the bag is provided a second removable coupling having a male part having a male end extending through an opening in the upper portion of the bag and a collar which abuts an inner side of the bag when the male end is fully inserted therethrough. A female part of the second removable coupling is removably connected to the first male end in a manner to sealably connect and sandwich a part of the upper portion between the collar and female part. A one way check valve is operably connected to the second removable coupling. A pressurized inert gas supply which is of a first predetermined molecular weight, e.g. such as stored compressed $CO2$, is communicably connected to the first male coupling by way of an automatically controlled valve. An explosive gas detector is operably disposed inside the bag and in communication with a processor which in turn is controllably connected to the automatically controlled valve such that when the explosive gas detector detects gas levels of an explosive type gas and of a second predetermined molecular weight different than the first predetermined molecular weight and at level to present a risk, it sends a signal to the processor which causes actuation of the automatically controlled valve to open and release the inert gas into the bag which in turn drives the explosive gas out through the one way check valve by means of the different molecular weights.

By so providing, the invention reduces and/pr prevents spontaneous ignition and/or explosion of stored biosolids materials. It is contemplated that there a various types of sensors or detectors can be employed. These can be configured to determine a critical threshold for explosive type gases that are well known to those skilled in the art.

BRIEF DESCRIPTION OF DRAWING

FIG. 1 depicts a biosolids storage system according to a preferred embodiment of the invention.

DETAILED DESCRIPTION OF PREFERRED EMBODIMENT

Referring now to the drawing, the biosolids storage system of the invention is generally designated by the numeral 10. The system 10 reduces and/or prevents the risk of spontaneous ignition and/or explosion of an explosive atmosphere of biosolids material 11.

The system 10 includes a biosolids bag 12 for containing biosolids material 11, such as fertilizer. Such biosolids material fertilizer contain organic components of biosolids can improve soil structure and its ability to hold water. Nitrogen, phosphorus, potassium, trace nutrients, and lime in biosolids can aid plant growth, and the organic matter in biosolids helps soil to retain the nutrients and make them more available to plants. Hence, these are valuable to the farming communities. The biosolids material 11 must be handled in accordance with Federal Part 503 rule and any state and local regulations. Under Part 503, biosolids that are disposed in a solid waste landfill, however, must be disposed according to 40 CFR Part 258 requirements.

The bag 12 can be a long (e.g. 10 meter continuous bag) poly or plastic bag for odor containment and spillage control of the biosolids material 11. The bag 12 is commonly sealed at the site once the biosolids material 11 is inserted therein in order to trap the material and odors, cutting down development of bacteria and fungus spores. The bag 12 can be of a suitable length and dashed lines represent a length may be varied.

However, prior to filling and containment, the invention provides for connecting to a lower portion 14 of the bag 12 a first removable coupling 16 having a male part 18 having a male end 20 extending through an opening 22 in the lower portion 14 of the bag 12 and a collar 24 which abuts an inner side 26 of the bag 12 when the male end 20 is fully inserted therethrough. A female part 28 is removably connected to the first male end 20 in a manner to sealably connect and sandwich a part 23 of the lower portion 14 between the collar 24 and female part 28. To an upper portion 30 of the bag 12 is provided a second removable coupling 32 having a male part 34 having a male end 36 extending through an opening 38 in the upper portion 30 of the bag 12 and a collar 40 which abuts inner side 26 of the bag 12 when the male end 36 is fully inserted therethrough. A female part 42 is removably connected to the male end 36 in a manner to sealably connect and sandwich a part 39 of the upper portion 30 between the collar 40 and female part 42. A one way automated check valve 50 is operably connected to a the second removable coupling 32.

A pressurized inert gas 52 is of a first predetermined molecular weight, e.g. such as stored compressed CO2, in a pressurized supply tank 53 is communicably connected to the first male coupling 16 by way of an automatically controlled valve 54. One or more explosive gas detector 56 is operably disposed inside the bag 12 and in communication with a processor 58 which in turn is controllably connected to the automatically controlled valve 54 such that when the explosive gas detector 56 detects gas levels of an explosive type gas which is of a second predetermined molecular weight different than the first predetermined molecular weight and at level to present a risk, the processor 58 causes actuation of the automatically controlled valve 54 to open and release the inert gas 52 into the bag 12 which in turn drives the explosive gas out through the one way check valve 50 by means of the different molecular weights.

In addition, the invention can additionally employ and additional air mover(s) which can be operatively to the system 10 by way of connecting to the couplings to assist in moving inert gas into the bag 12. The inert gas 52 neutralizes the reactive nature of the atmosphere by replacing the atmosphere present in the bag 12 with a non-explosive atmosphere, for example by replacing the air with a gas such as nitrogen or carbon dioxide.

The detector 56 can be battery powered and wirelessly communicate to processor 58 which is equipped with a wireless receiver to receive signals indicating environmental conditions corresponding to the atmospheric air within the bag 12 which is susceptible to ignition and/or explosion.

While the invention provides for and embodiment, it is apparent to those skill in the art that there are various modifications, derivations, and improvements which will be apparent. Accordingly, search modifications, derivations, and improvements should be afforded within the appended claims hereto.

What is claimed is:

1. A system for reducing and/or preventing the risk of spontaneous ignition and/or explosion of an explosive atmosphere of a biosolids material fertilizer, which includes:
   a biosolids bag for containing biosolids material fertilizer, having a first end portion having a first part thereof defining a first opening and a second end portion having a second part thereof defining a second opening, and said bag being sealable once biosolids are disposed therein;
   a first removable coupling connected to said lower portion of said bag, said first removable coupling having a male part having a male end extending through said first opening and a collar which abuts an inner side of said bag when said male end is fully inserted therethrough, a female part removably connected to said male end in a manner to sealably connect and sandwich said first part of said first portion between said collar and said female part;
   a second removable coupling connected to said second portion of said bag, said second removable coupling having a male part having a male end extending through said second opening and a collar which abuts said inner side of said bag when said male end of said second removable coupling is fully inserted therethrough, a female part of said second removable coupling removably connected to said male end of said second removable coupling in a manner to sealably connect and sandwich said second part of second portion between said collar and said female part of said second removable coupling;
   a one way check valve operably connected to said second removable coupling;
   a pressurized inert gas supply of a first predetermined molecular weight communicably connected to said first male coupling by way of an automatically controlled valve;
   an explosive gas detector operably disposed inside said bag for generating a signal indicative of explosive gaseous conditions having met a predetermined level within the bag; and
   a processor in communication with said detector to receive said signal and which in turn is connected to an automatically controlled valve such that when receiving said signal indicative of an explosive gas of a second predetermined molecular weight different than the first predetermined molecular weight and at level to present a risk, said processor causes actuation of the automatically controlled valve to open and release said inert gas into said bag which in turn drives said explosive gas out through said one way check valve by means of the different molecular weights.

2. The system of claim 1, wherein said processor and said detector communicate wirelessly.

3. The system of claim 1, wherein one of said first end portion and said second end portion is an upper end portion and one is a lower end portion.

* * * * *